(12) United States Patent
Armbruster (10) Patent No.: US 7,943,579 B2
(45) Date of Patent: May 17, 2011

(54) OSTEOGENIC IMPLANT MATRICES AND ENDOSSEOUS TOOTH IMPLANTS WITH IMPROVED OSTEOINTEGRATION PROPERTIES

(75) Inventor: Franz Paul Armbruster, Bensheim (DE)

(73) Assignee: Immundiagnostik AG, Bensheim (DE)

( * ) Notice: Subject to any disclaimer, the term of this patent is extended or adjusted under 35 U.S.C. 154(b) by 1079 days.

(21) Appl. No.: 11/579,039

(22) PCT Filed: May 2, 2005

(86) PCT No.: PCT/EP2005/004746
§ 371 (c)(1), (2), (4) Date: Jan. 23, 2007

(87) PCT Pub. No.: WO2005/104988
PCT Pub. Date: Nov. 10, 2005

(65) Prior Publication Data
US 2007/0233271 A1    Oct. 4, 2007

(30) Foreign Application Priority Data
Apr. 30, 2004    (DE) .......................... 10 2004 021 244

(51) Int. Cl.
*A61K 38/00*    (2006.01)

(52) U.S. Cl. ...................................................... 514/16.7
(58) Field of Classification Search ........................ None
See application file for complete search history.

(56) References Cited

U.S. PATENT DOCUMENTS

| | | | |
|---|---|---|---|
| 6,458,763 B1 * | 10/2002 | Peterson et al. .................. 514/8 |
| 2004/0109937 A1 | 6/2004 | Jennissen et al. ............. 427/2.26 |
| 2005/0064007 A1 * | 3/2005 | Steinemann et al. ......... 424/423 |
| 2005/0107887 A1 * | 5/2005 | Knothe Tate et al. ........ 623/23.5 |

FOREIGN PATENT DOCUMENTS

| | | |
|---|---|---|
| EP | 1 084 719 | 3/2001 |
| WO | WO 94/13310 | 6/1994 |
| WO | WO 99/08730 | 2/1999 |
| WO | WO 99/16792 | 4/1999 |
| WO | WO 02/085250 | 10/2002 |

* cited by examiner

*Primary Examiner* — Michael Pak
(74) *Attorney, Agent, or Firm* — James C. Lydon (57) ABSTRACT

Implant articles with improved osseointegrating properties, osteogenic implant materials, and process of inducing differentiation of mesenchymal stem cells, proliferation of osteoblast and attachment of cells to implant surface, comprising the step of impregnating the surface with a solution containing osteoactive bone sialoprotein, recombinant human bone sialoprotein, recombinant His-Myc-Ek-BSP or substantive fragments thereof that have not been in contact with serum containing complement factor H or any other BSP processing material.

9 Claims, 5 Drawing Sheets

OSTEOGENIC IMPLANT MATRICES AND ENDOSSEOUS TOOTH IMPLANTS WITH IMPROVED OSTEOINTEGRATION PROPERTIES

FIELD OF THE INVENTION

The invention relates to implant materials with improved osteointegration properties, osteogenic matrices and endosseous tooth implants for a fixed dental prosthesis.

BACKGROUND OF THE INVENTION

The stability of bone implants and particularly endosseous tooth implants depends greatly on the ingrowth properties of the implant material. Implant articles and synthetic bone matrices are therefore often provided as highly porous structures of bone-mimetic materials with bioactive coatings. The osteointegration process of an implant into the surrounding bone is complex and involves adaptive cellular responses such as differentiation, migration, attachment, proliferation, extracellular matrix synthesis and finally mineralization of the matrix. Bone sialoprotein (BSP), a phosphorylated 70-80 kDa phosphorylated glycoprotein, is beside osteocalcin and osteonectin the major non-collagenous protein in the extracellular matrix of bone (Fisher L W, Termine J D 1985 *Non-collagenous proteins influencing the local mechanisms of calcification*, Clin Orthop 200:362-385; Marks S C, Popoff S N 1988 *Bone cell biology: The regulation of development, structure, and function in the skeleton*. Am J Anat 183:1-44). The expression of BSP coincides with initial bone mineralization (Hunter G K, Goldberg H A 1993 *Nucleation of hydroxyapatite by bone sialoprotein*. Proc Natl Acad Sci USA 90:8562-8565; Hunter G K et al. 1994 *Modulation of crystal formation by bone phosphoproteins: Role of glutamic acid-rich sequences in the nucleation of hydroxyapatite by bone sialoprotein*. Biochem J 302:175-179; Hoshi K, Ozawa H 2000 *Matrix vesicle calcification in bones of adult rats*. Calcif Tissue Int 66:430-434). Moreover, it was shown that BSP is osteoinductive when coated onto femoral implants (OToole G C et al, 2004, *Bone sialoprotein-coated femoral implants are osteoinductive but mechanically compromised*. J Orth Res 22:641-646.).

U.S. Pat. No. 5,478,237 (Ishikawa) describes a titanium implant provided with a layer of bioactive hydroxyapatite, WO 02/078759 (Stratec Medical AG et al.) an implant with a porous metal oxide layer comprising amorphous and nanocrystalline calcium phosphate and hydroxyapatite, WO 02/085250 (KERAMED GmbH) an implant provided with a metabolically activating coating comprising resorbable calcium phosphate phases as well as adhesion and signal proteins such as bone sialoprotein (BSP), bone morphogenic proteins (BMP), fibronectin, osteopontin (OPN), ICAM-I VCAM und functional derivatives thereof. Other metallic implants of this kind are described in EP 1 166 804 A2 (Merck, Darmstadt) and WO 99/08730 (Children's Medical Center Corporation). DE 100 37 850 A1 (Jenissen H) and WO 03/059407 A1 (Straumann Holding A G) describe the application of ubiquitin, transforming growth factor (TGF) and other systemic hormones such as osteostatin, osteogenie and osteogrowth peptide (OGP) on implants. US 2004-0033249 teaches metal implants with a biomimetically produced bone-analogous coating comprising a collagen matrix mineralised with calcium phosphate, EP 1 442 755 A1 (Depuy Products) a bioactive ceramic surface coating into which biological agents are incorporated, amongst others, the osteogenic proteins OP-1, BMP-7 and non-collagenous bone matrix proteins. Further mentioned have been fibroblast growth factor (FGF), transforming growth factor-β (TGF-β), platelet-derived growth factor (PDGF), insulin growth factor (IGF) and family members of the foregoing. The osteointegration activity of these bioactive molecules, however, is mere speculation because their osteointegrating activity cannot be measured, neither in vitro nor in vivo. Bone-mimetic surface layers on implant articles suffer from the disadvantage that they loosen from the substrate with time which affects in particular the long-term stability of the implant. On the other hand there is strong evidence that metal implants inhibit the necessary differentiation of the mesenchymal stem cells to osteoblasts especially when the implants have worked surfaces and thus bear small abrasion particles (Wang et al., J. Orthopedic. Res., 2002, 20, 1175-84).

In practice, aseptic loosening of endosseous implants remains an unsolved problem, long-term stability too and osteointegration properties of the implant in general. Despite the known bioactive coatings there is regularly a considerable time lag between surgery and commencement of the bone healing processes so that endosseous tooth implant must remain unloaded for months after placement before they withstand the typical pressure, shear and tensile forces.

SUMMARY OF THE INVENTION

It is an object of the present invention to provide an implant material which promotes, rather than retards, differentiation and proliferation of osteoblasts for osseous growth and osteointegration. A further object of the invention is to provide a titanium or zirconium material for implant articles and bone repair matrices to which osteoblasts can adhere more strongly and more promptly after placement.

The invention provides an implant material treated with bone sialoprotein or substantive fragments thereof that have not been in contact with serum or cannot bind complement factor H, respectively.

A preferred embodiment of the invention relates to an implant material which has been coated with bone sialoprotein, recombinant human bone sialoprotein, recombinant His-Myc-Ek-BSP or substantive fragments thereof which have not been in contact with serum proteins and in particular complement factor H.

The substantive fragments of human bone sialoprotein comprise the RGD sequence which is known to be relevant for the binding of BSP and BSP fragments to the integrin receptor. The substrate of implant material according to the invention is made of a material selected from titanium, titanium oxide, zirconium, zirconia, tantalum, tantalum oxide, niobium, niobium oxide, magnesium, ceramic, alloys thereof and stainless steel. Preferred implant materials are SLA, CPT, ANOX, TICER while many more commercially available implant materials can be used.

The implant material is preferably coated with hydroxyapatite and/or amorphous or nanocrystalline calcium phosphate. Moreover, other bioactive proteins as mentioned in the background section of this application can be used in the surface coating. The implant material of the present invention has preferably a rough, machined or porous surface structure. When a porous implant material is used the surface structure preferably has pores of 50 to 200 μm diameter and a pore density of $10^5$ to $10^7$ pores per square millimetre.

The preferred implant article of the invention is an endosseous tooth implant for fixed dental prosthesis, a bone prosthesis, or a bone repair article or matrix.

A further aspect of the invention is a process for improving the osteointegration properties of implant articles, which comprises the step of impregnating the article surface with a solution containing BSP, recombinant human BSP, recombinant His-Myc-Ek-BSP or substantive fragments thereof that have not been in contact with serum containing complement factor H. A preferred embodiment of this process relates to the differentiation of mesenchymal stem cells, proliferation of osteoblasts and attachment of cells to an implant material, which comprises the step of impregnating the surface with a solution containing bone sialoprotein, recombinant human BSP, His-Myc-Ek-BSP or substantive fragments thereof.

DETAILED DESCRIPTION OF THE INVENTION

The invention provides a novel extracellularly non-modified BSP-coated implant material which promotes differentiation of mesenchymal stem cells to osteoblasts, induces osteoblast migration to the implant surfaces as well as osteoblast proliferation and provides for stronger adherence of the osteoblasts cells to the implant surface. The successful attachment to the artificial surface is the prerequisite for inducing new bone formation locally at the site of implantation. To improve the osteogenic properties and the biocompatibility of implant materials various protein coatings were investigated for this purpose, mainly collagen, fibronectin, vitronectin or mixtures of natural extracellular matrix proteins (Sodek J, McKee M D 2000 *Molecular and cellular biology of alveolar bone*. Peridontol., 24:99-126; Meyer U et al, 1998, *Attachment kinetics, proliferation rates and vinculin assembly by bovine osteoblasts cultured on different pre-coated artificial substrates*. J Mater Sci-Mater Med 9:301-307; Lacouture M E et al., 2002 *A comparison of type I collagen, fibronectin, and vitronectin in supporting adhesion of mechanically strained osteoblasts*. J Bone Miner. Res 17:481-492; Salih E et al, 2002, *Natural variation in the extent of phosphorylation of bone phosphoproteins as a function of in vivo new bone formation induced* by demineralized bone matrix in soft tissue and bony environment. Biochem J. 364:465-474). Also BSP was found to be osteoinductive in bone repair (Wang J et al, 2004 *Bone Sialoprotein elicits biomineralization and ossification in a bone defect model*. J Bone Miner. Res. 19: 221 Abstract) and was sufficient to achieve healing in critical defects (Wang M L et al., 2002, *Titanium particles suppress expression of osteoblastic phenotype in human mesenchymal stem cells*. J Orth Res 20:1175-1184). By comparison of type I collagen, fibronectin, and vitronectin in supporting adhesion of mechanically strained osteoblasts it was revealed that the major factor governing strain resistance was the number of the integrin-extracellular matrix attachments when the number of molecules available for attachment was limited (Lacouture M E et al., 2002 *A comparison of type I collagen, fibronectin, and vitronectin in supporting adhesion of mechanically strained osteoblasts*. J Bone Miner Res 17:481-49220). At a low protein-coating density collagen supported the highest attachment rate followed by fibronectin and vitronectin. At higher concentrations vitronectin supported the highest attachment rate after 24 hours in vitro. Notwithstanding, the key to implant success is the initial healing process (Lekic P et., 1996 *Osteopontin and bone sialoprotein expression in regenerating rat periodontal ligament and alveolar bone*. Anat Rec 244:50-58). The large surface area of rough materials leads to an initially delayed cell proliferation. The initial delay at the rough TICER surface can be compensated according to the invention by a BSP-coated surface. In this connection it was found that BSP occurs physiologically in osteoinducing and inactive forms. The deposition of BSP represents the first step of bone formation in ectopic transplantation systems in vivo (Riminucci M, Bianco P, 2003, *Building bone tissue: matrices and scaffolds in physiology and biotechnology*. Braz J Med Biol Res 36:1027-1036). So efforts have been made as to induce the expression of BSP by inductive agents (Chou et al., 2005 *The effect of biometric apatite structure on osteoblast viability, proliferation and gene expression*. Biomaterials 26:285-29529). We have now found that BSP seemingly undergoes extracellular maturation or masking processes which reduce the differentiating and proliferating potential of BSP on mesenchymal stem cells and osteoblasts with time. In essence it was found that recombinant BSP isolated from cell culture has proven to be much more effective and has physiologically other potential than isolated BSP which has been subject to extracellular modifications. It will be necessary to examine the deactivation of BSP by the binding of complement factor H to BSP and by the calcification and mineralization of the extracellular matrix.

According to recent hypotheses, BSP is supposed to protect trophoblasts and BSP-producing tumours from attack by the immune system. Namely, BSP binds with high affinity the factor H of the complement system, which is known to restrict the alternative path of the complement lysis. BSP can further specifically bind to the integrin receptors on the cell surface through its own recognition sequence (arginine-glycine-aspartate, RGD). In the case of expression of BSP the cells are then supposed to bind the factor H in the blood and in the tissue fluids to their cell surfaces, or concentrate it around them. Such a protection of BSP from the complement system of the blood of the mother is suspected also for the trophoblasts in the placenta (Fedarko N. S. et al. Factor H binding of BSP and osteopontin enables tumor cells evasion of complement-mediated attack, in J. Biol. Chem., 200, 275, 16666-16672; WO 00/062065).

Further there is also suspected a function of BSP in angiogenesis. Along with the adhesion of osteoclasts and osteoblasts to the bone matrix—through the binding of the RGD recognition sequence in the matrix to the alpha(v)beta(3) integrin receptors on the cell wall—it is also observed that the adhesion, dissemination and orientation of the endothelial cells is probably mediated by BSP. Namely, blood vessel formation around a tumor occurs in parallel with the BSP expression in the tumor cells (Bellahcne A et al., *Bone sialoprotein mediates human endothelial cell attachment and migration and promotes angiogenesis*, in Circ. Res. 2000, 86(8), 885-91).

BSP thus stands at the centre of events in the formation of bone matrix. The binding of BSP via the RGD sequence to vitronectin or integrin receptors of epithelial cells can be restricted by antagonists. In accordance with the invention, it is therefore taught to have recombinant BSP or fragments of recombinant BSP, preferably comprising the RGD sequence, as osteoactive substance for the support of the repair of damaged bone and connective tissue. WO 94/13310 teaches a composition having a BSP binding protein of staphylococcus aureaus as active ingredient. It therefore also contemplated to have the recombinant osteoactive BSP, or essential fragments thereof, bound to the implant surface via linker molecules and linker proteins since in body fluids free BSP is bound by complement factor H with high affinity and because active BSP can bind to various receptors. This is in line with the observation that different antibodies are obtained with recombinant/synthetic BSP and BSP isolated from bones, which antibodies failed to recognise any BSP in human serum (Fisher, L. W. et al., *Antisera and cDNA probes to human and certain animal model bone matrix noncollagenous proteins*. Acta Orthop Scand Suppl., 1995, 266, 61-655), in contrast to antibodies obtained with recombinant BSP (Stubbs J T 3.sup.rd et al., *Characterization of native and recombinant bone sialoprotein: delineation of the mineral-binding and cell adhesion domains and structural analysis of the RGD domain*. J. Bone Miner. Res. 1997 12(8), 1210-22). The significantly larger factor H molecule of 150 kDa probably masks the smaller BSP (of ca. 65 kDa) to such an extent that antibodies or a receptor cannot bind. Further, factor H is present in excess in the serum (0.5 mg factor H/mL in comparison to BSP with <20 ng/ml Serum in the case of healthy persons and max. 160 ng/ml in the case of tumor patients). It has been claimed that due to the binding with factor H immunological direct determination of BSP in body fluids is impossible without special sample preparation (Fedarko N. S. et al., *Factor H binding of bone sialoprotein and osteopontin enables tumor cell evasion of complement-mediated attack*, in J. Biol. Chem., 200, 275, 16666-16672).

Figure 1:
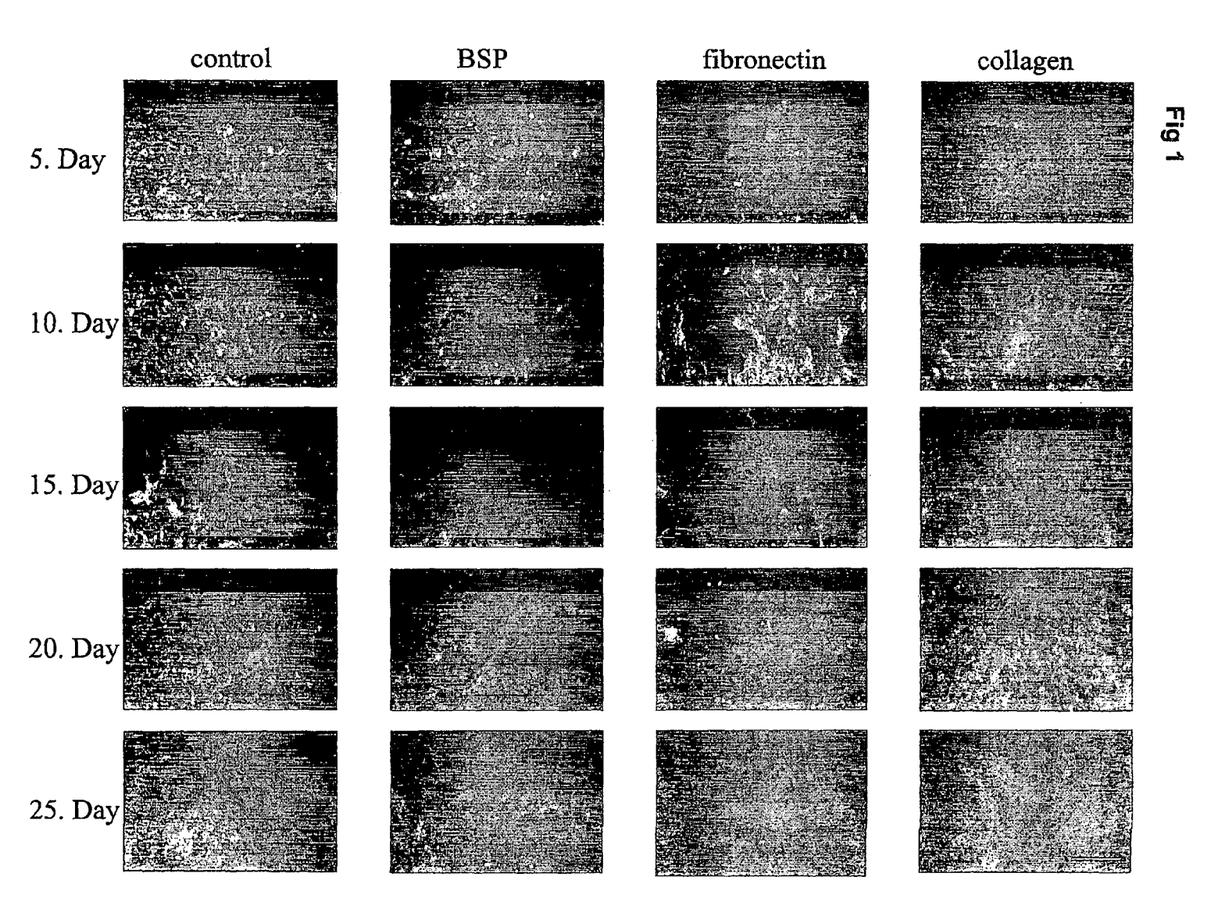
FIG. 1 are light microscopic photographs showing immunhistochemically stained cells settled on the pre-coated surface of the implant material TICER at day 5 to 25: red=expressed BSP, blue=DAPI-staining; and green=patterns of CD90; bar 100 μm.
Figure 2:
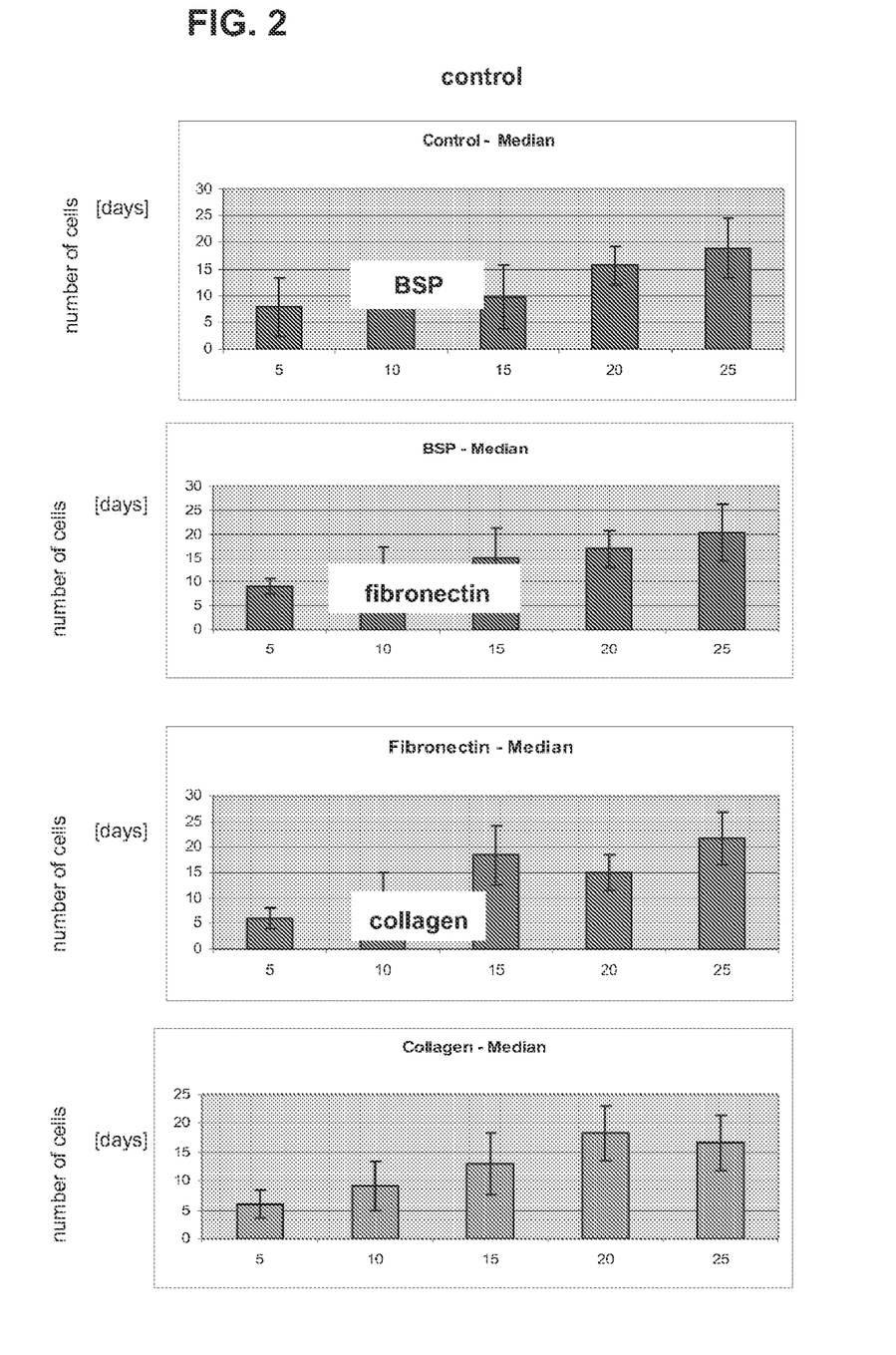
FIG. 2 is a schematic diagram showing the development of the number of cells expressing BSP (median values) from day 5 to 25.
Figure 3:
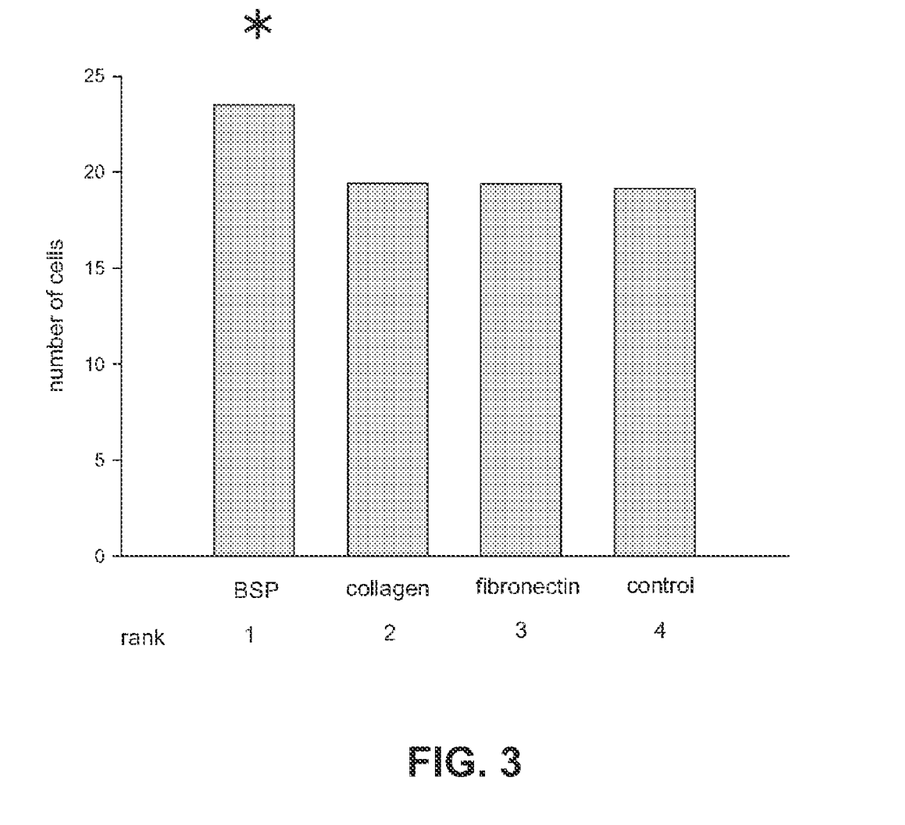
FIG. 3 is a schematic diagram with the median values of the number of cells expressing BSP at day 3; the number of cells settled at the BSP-coated surface of TICER is higher than at all other surfaces.

The experimental data indicates that low concentrations of recombinant BSP and osteoactive BSP fragments are sufficient to induce differentiation of mesenchymal stem cells and initial attachment of osteoblasts as shown by FIGS. 1-3. Differentiation and settlement of cells is particularly no longer retarded in case of roughened and worked titanium surfaces such as TICER. Moreover, it noted that a osteoactive BSP coating can be easily applied into the pre-formed pores of a titanium matrix or implant surface as a firm attachment of the protein can be achieved by impregnating the bone repair matrix or implant surface with a suitable osteoactive rBSP protein solution followed by subsequent drying. The rBSP protein is highly acidic and can thus form hydrate bridges with hydroxy surface groups present on $Ti/TiO/TiO_2$. By applying the BSP coating directly on the titanium surface and in the pores of a titanium matrix a rapid attachment of the osteoblasts and ingrowth of the surrounding bone tissue into the matrix is obtained—and in particular, bone formation is not inhibited due to the abrasive metal particles on the surface. In other words, a mineralized or bony osteointegration of the implant can be achieved when the osteoblasts attach and grow indeed into the pores of the implant, which pores should preferably have a diameter size of 10 to 1000 μm, more preferably, 20 to 500 μm, most preferred 50 to 200 μm.

The titanium implant may have a titanium oxide surface (brookite, rutile or anastase) and additionally a biomimetic surface of hydroxyapatite and/or calcium phosphate phases of amorphous and nanocrystalline calcium phosphate phases, if required. The pore sizes are preferably around 100 μm (50 to 200 μm) and the pore density is about $10^5$ to $10^7$ pores per square centimeter.

When the surface is rBSP-coated, there is no longer a gap between titanium implant and newly formed bone matrix. The coating with extracellularly non-modified bioactive BSP and BSP-fragments further achieves that the surrounding bone tissue can grow after placement of the implant or repair matrix into the porous titanium structure.

The implant material of the invention is characterized by an effective amount of osteoactiv rBSP or synthetic fragments thereof, preferably in an effective amount of 0.01 to 10 $μg/cm^2$, so that the material carries about 100 effective molecules per square micrometer. The extracellularly osteoactive BSP is preferably recombinant human BSP from MDP-cells. The BSP can be coated together with osteopontin, osteonectin, fibronectin, collagen or pro-collagen. The implant material or implant matrix is preferably made of a titanium material, a titanium alloy, zirconium or zirconia, while also ceramics or composite materials are possible. Other materials contemplated are tantalum, tantalum oxide, aluminum, alumina, vanadium oxide, magnesium, stainless steel and other alloys.

Examples

The invention is based on discoveries made by comparing BSP-coated, collagen-coated, fibronectin-coated, recombinant BSP-coated and non-coated implant materials in supporting the development of adult human maxillary bone at day 3, 5, 10, 15, 20 and 25 in vitro. All of the procedures used in the present experiments were approved by the Ethics Committee of the University of Leipzig. The rules of the Declaration of Helsinki 1964 (NIH publication no. 86-23, revised 1985) were followed.

Tissue Preparation

Human maxillary bone samples without any clinical or radiographic evidence of pathology were obtained from two donors undergoing dental surgery at the Department of Oral-, Maxillar-, Facial- and Reconstructive Plastic Surgery, University Hospital of the University of Leipzig. The bone samples were placed in a sterile tube containing sterile 0.05 M phosphate-buffered saline (PBS), pH 7.4, containing 10 000 IU/mL penicillin, 10000 μg/mL streptomycin (PromoCell, Germany). The samples were processed under sterile conditions thereafter. The maxillary bones were cut into small pieces of 0.1 to 0.2 cm, rinsed several times with PBS, pH 7.4, incubated with 0.25% collagenase type IV (166 U/mg, Biochrom AG, Germany) at 37° C. for 2-3 hours, washed and then cultured in Dulbecco's modified Eagle's medium (PromoCell, Germany) supplemented with 10% fetal bovine serum (PromoCell, Germany) at 37° C. in a humidified atmosphere of 5% $CO_2$ in air. The medium was changed twice a week. Subcultured cells were seeded with a density of 4000 cells per well in six-well plates. First passage cultures were used in all experiments.

Implants

The dental implant material TICER and the technical material glimmer were used.

TICER (ZL-Microdent, Germany) is based on a material developed by Graf H L, (1997 in *Zur Entwicklung und Char-* akterisierung eines neuen Implantatsystems. Habilitationsschrift, Leipzig) and consists of titanium with hydroxyapatite ceramic and therefore roughened surface for better attachment of bone to metal (Hulbert S F et al., 1970, *Potential of ceramic materials as permanently implantable skeletal prostheses*. J Biomed Mater Res 4:433-456; Schwartz Z et al., 1999, *Implant surface characteristics modulate differentiation behaviour of cells in the osteoblastic lineage*. Adv Dent Res 13:38-48.). In contrast, glimmer has a total smooth surface. Other implants tested were CPT (commercially pure titanium), ANOX, ITI/SLS.

The implant samples (10×30×1 mm) were coated in BSP, collagen and fibronectin solutions and then placed in the cell culture six-well plates. This was achieved by dissolving 10 μg BSP (His-Myc-Ek-BSP, Immundiagnostik, Bensheim, Germany) and 10 μg fibronectin (Biochrom AG, Germany), respectively, in 1 ml sterile phosphate buffered saline (pH 7.2, 0.9M). Collagen (Cohesion, USA) was used as VITROGEN 1% (bovine dermal collagen dissolved in 0.012 N HCl). Twenty-four implants were then incubated with 300 μl solution of BSP or fibronectin or collagen for 2 hours. The coated implants were removed from the coating solution and allowed to dry at room temperature under sterile conditions for 12 hours. Thereafter the cells were seeded and fixed at day 3, 5, 10,15, 20 and 25.

Additional experiments were performed to compare human BSP isolated from bone and recombinant BSP (His-Myc-Ek-BSP) under the same conditions as described above. The native BSP was purified according to Karmatschek et al., 1997, *Improved purification of human bone sialoprotein and development of a homologous radioimmuno-assay*, Clin. Chem., 43:2076-2082. The recombinant BSP was isolated according to the method described by Wuttke et al. (Wuttke et al, 2001, *Structural characterization of human recombinant and bone-derived bone sialoprotein*. J Biol Chem 276:36839-36848). In essence, the complete cDNA for human BSP (without signal peptide) was amplified by means of PCR and cloned in the episomal eucaryotic expression vector pCEP-Pu (Kohfeldt E et al., *Properties of the extracellular calcium binding module of the proteoglycan testican*, in FEBS Lets. 1997, 414(3) 557-61). The expression constructs were introduced by means of liposome mediated stable transfection (FUGENE.™. transfection reagent of the company Roche) inter alia into the embryonic kidney cell line EBNA-293 and the human breast cancer cell line MCF-7. Transient cells were cultivated, 48 hours after transfection for two days in serum-free medium so that the proteins in the FCS could not react with the expressed rBSP and interfere with the purification of the recombinant BSP. BSP expressing cells were, after attainment of confluence, cultivated under serum free conditions. Under these conditions only EBNA-293 cells could survive longer than 2 to 4 days. The expression of the recombinant BSP was monitored through SDS-PAGE and immunoblots. The investigation of serum-free cell culture supernatants yielded with all these cell lines a positive signal in the Western Blot, both with reference to BSP and also the presence of the various tags.

2.5 liter serum-free culture supernatant of the transfected MCF-7 cell line was purified via a Sepharose™ column and there was obtained therefrom 250 μg homogeneous His-myc-EK-BSP. The so purified expression product was partially glycosylated, however had no glycosylation at threonine 125.

The amino acid sequence of human BSP contains four potential N-glycosylation sites at the positions 88 (NTT), 161 (NCT), 166 (NST) und 174 (NGS). For O-glycosylation there is known no comparable consensus sequence. All identified N-glycane structures could be found both on the BSP isolated from bones and on the recombinant EBNA-293 BSP. There were however differences in the percentage proportion of the respective structures in the total N-glycanes. Thus, the main proportion of the BSP N-glycanes in bones was of triantenary structures (58%) and in the EBNA cell line of tetraantenary structures (48%). For localization of the O-glycosylation sites of recombinant BSP, the O-glycanes were removed by means of sequential digestion of the protein with neuraminidase, β-galactosidase and β-N-actylhexosaminidase, down to the core-GalNAc. The partially deglycosylated protein was then split by treatment with trypsin and V8 protease into peptide fragments. By means of MALDA-TOF mass spectrometry the masses of the peptides were determined and a part of the peptides sequenced by means of PSD-MALDI-TOF mass spectrometry. Of these, in the recombinant BSP, the threonines in the sequence DATPGTG are O-glycosylated. With bone BSP there was effected a third O-glycosylation. With recombinant BSP no third glycosylation site is present. Probably, this glycosylation site lies on the TGLAA-BSP part structure.

Immunocytochemistry

Cell cultures were fixed with 4% paraformaldehyde in PBS for 15 minutes each and rinsed four times in PBS.

Cells on the surface of the implant discs were incubated with 10% normal goat serum (Vector, Burlingame, USA) diluted in PBS for two hours. Thereafter the cells were simultaneously incubated with the primary antibody against BSP (1:100, mouse monoclonal anti-human BSP, Immundiagnostik, Bensheim, Germany) and the primary antibody against fibroblasts (monoclonal anti-human CD90, FITC-conjugated, DIANOVA, Hamburg, Germany). The cells were incubated with 1:100 antibody dilutions overnight at +4° C. (Saalbach A et al, Cell Tissue Research, 1997, 290, 593-599).

After several rinses in PBS, cells were incubated for two hours with 1:50 dilution of goat-anti-mouse-Cy3 (Jackson ImmunoResearch) in PBS containing 4% bovine serum albumin (Serva AG, Germany). After several washes with PBS the cell preparations were counterstained using 4,6-diamidino-2-phenylindol (DAPI), dried and cover slipped.

Measuring Procedure

We counted the DAPI-BSP labelled cells on the surface of the implants both on the borderline as well as in the middle of the sample. Three to ten successive sections were screened at 400× magnification using a measuring frame (350 μm×230 μm). Exclusively the values of analogous parts were used for averaging. The interactive measurements were carried out using the software of the Kontron-Videoplan-System (Kontron, Zeiss, Germany) and the "frozen image tool". The system software of the Videoplan provided the mean value (average±standard deviation) and the median values for each file. The U-test was used to compare the data sets of the different files and to analyse the level of significance of the differences among the various coated surfaces. For rapid approximation we used ranks in a test of Wilcoxon F (1945) Biometrics 1:80-83 und Wright C (1952), Biometrics 8:33-41.

AFM Microscopy

The atomic force microscope (AFM) moves a very small sharp tip attached to a soft cantilever, which acts as a spring, in a raster pattern over the sample surface. Deflections in the tip that correspond to surface topography are recorded. The AFM can be operated in air and liquids. In routine diagnosis, it is often desirable to minimize cantilever deflections in order to prevent the sample experiencing from too large and potentially damaging forces. For this procedure, a feedback loop is used to adjust the sample height while imaging. This analysis was performed on an AFM (Topometrix Explorer) with 130

μm xy-scan range and 10 μm z-scanner. The AFM is mounted on top of an inverted microscope (Zeiss Axiovert 135) in order to select the region of interest on the sample surface. For observations of the specimen in ambient conditions soft cantilevers were utilized in constant force mode (sharpened microlevers, spring constant=0.02 N/m, tip radius<10 nm, Thermomicroscopes Sunnivale Calif. USA). The forces which were applied during AFM measurements were 10-20 nN in ambient conditions (Thalhammer S et al., 2001, *Atomic Force Microscopy with high resolution imaging of collagen fibrils—A new technique to investigate collagen structure in historic bone tissues*. J Archeol Sei 28: 1061).

Results

The expression of BSP in cells (red colour) was first visualized at day 5 with exception of the cells at the fibronectin-coated surface (FIG. 1). Some of the cells were extremely large, especially at the recombinant BSP-coated implant surface. BSP was mostly localized within the non-mineralized matrix. First the morphology of the osteoblast-like cell was spheroidal changing to their typical polygonal morphology after one day (not shown). The fibroblast marker (green) indicated a co-localization of the expression of BSP and CD 90. In the control sample, the dominance of the green colour persisted until day 20. The distribution patterns of cells at the surfaces of the implants as revealed using DAPI varied widely. Examples are given in FIG. 1. Expression of BSP displayed a half-circular pattern at day 10 and 15. At day 20 and 25 cells were homogeneously distributed at the surface of the implant.

Cell countings revealed that most of surviving cells are settled on the surface of the BSP-coated implants. FIG. 2 displays the median values and the standard deviations indicating only small differences between the various samples. Significantly different values were found at day 3 and 5, exclusively. The test using rankings of the median values gives evidence for BSP-coatings at rank 1 followed by collagen (FIG. 3). The maximum of the expression of BSP corresponded to the maximal number of cells for each sample.

Figure 4:
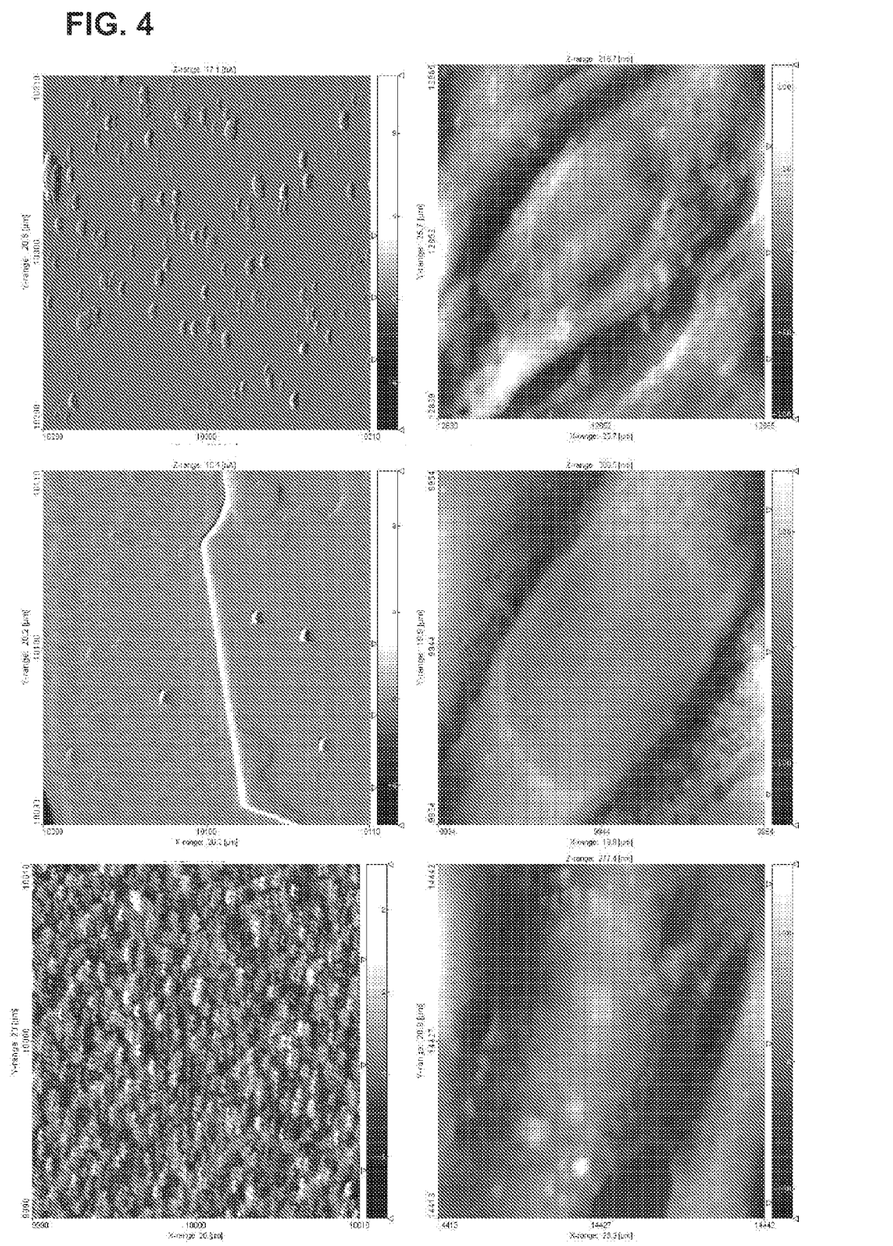
FIG. 4 are atomic force micrographs (left column) of a Ti glimmer surface coated with fibronectin (top), BSP (middle) and collagen (bottom) and atomic force microanalyses (right column) of the properties of the settled cells at the glimmer surface coated with fibronectin (top), BSP (middle) and collagen (bottom), at day 3.
Figure 5:
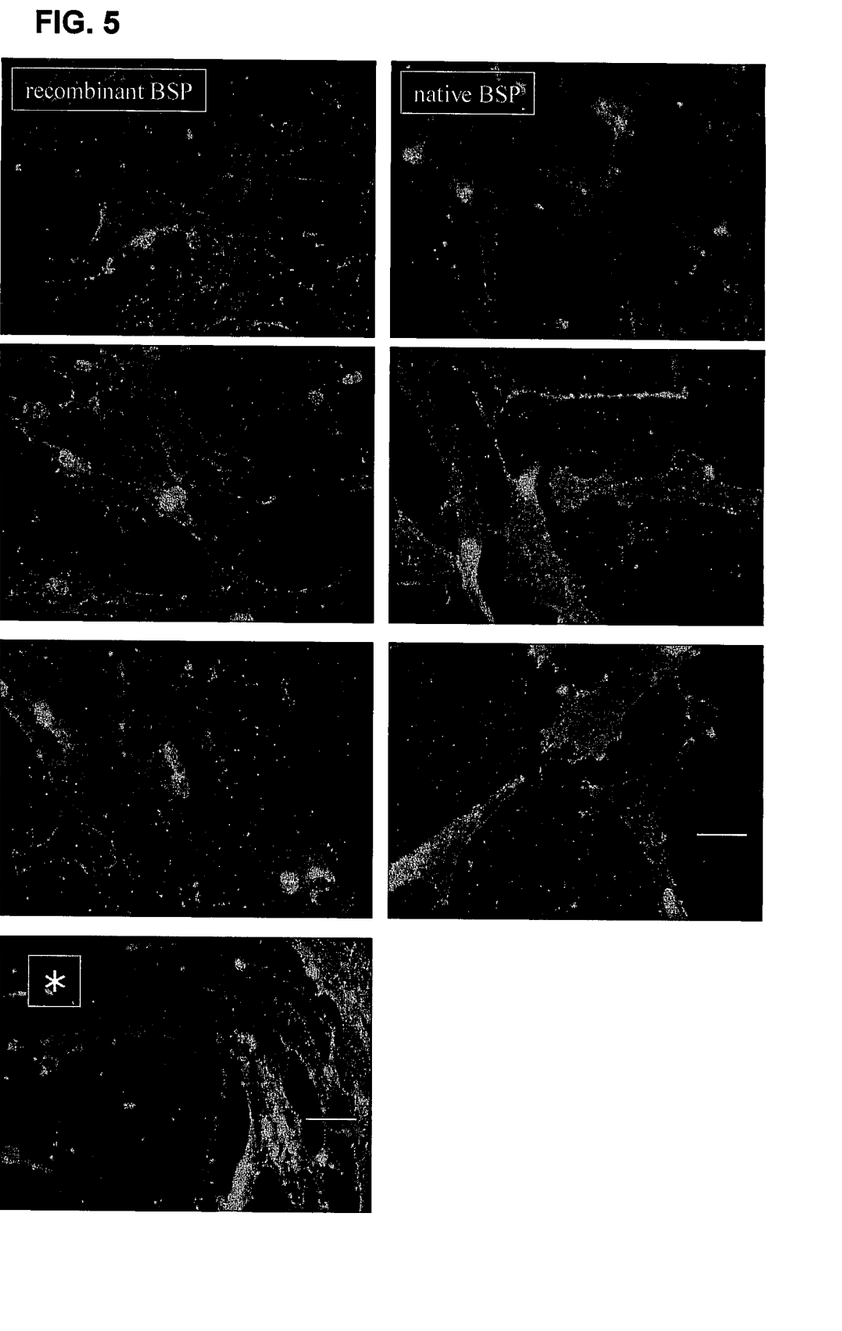
FIG. 5 are light microscopic photographs showing immunhistochemically stained cells settled on a pre-coated TICER surface: recombinant BSP (rBSP) induced a network-like growth of osteoblasts at day 3 (left column). When the surface was coated with native BSP, an isolated growth of single osteoblasts was observed at day 3 (right column); Bar 25 μm. Marked photograph*: right half-rBSP-coated glimmer; left half-non-coated Ti glimmer which lacks osteoblast like cells expressing BSP; Bar: 50 μm.

The advantage of the rBSP-coatings seems to be the early osteoinductive effect at day 3 and 5, which is lost in vitro at later days. On the other hand, the results of the atomic force microscopy revealed that the patterns of BSP-, collagen- and fibronectin-coatings differed widely when investigated without any cells (FIG. 4). The best results were found for collagen with a total homogeneous distribution pattern covering the whole surface and promoting the settlements of cells at the glimmer surface. The BSP-coating results in very few drop aggregations on the surface. Some more drop agreegation on the surface were revealed for fibronectin coating with the highest level of the z range. In summary we found osteoblasts with different soma sizes and features. The distribution patterns of settled cells were identical (FIG. 4). The influence of the BSP coating on the glimmer surface with discontinuously moistened surface is shown in FIG. 5* showing the borderline (see FIG. 4) of coated and non-coated region. The difference in both the number of cells and the expression of BSP is striking; the cells clearly have different properties and are in different developmental stages. When comparing the distribution of the cells on the glimmer surface and on surface of the dental implant material TICER, we found that the attachment of cells depends to high degree on the structure of the surface. However, when materials had identical surface structures BSP-coating clearly proved osteoinducing. Moreover, we compared coatings with native and recombinant BSP with regard to cell settlement. While we found no marked differences in the numbers of cells settled on the glimmer material, it is obvious that recombinant BSP promotes the differentiation of precursor cells into osteoblast-like cells as proven by the higher expression of BSP (FIG. 5). Moreover, osteoblast cells settling at the surface coated with recombinant BSP produced a network like structure whereas the same cells on a surface coated with native BSP solution stayed solitary. At an early attachment stage (day 3) osteoblasts displayed BSP in a punctuated pattern at their cell margins. Later on, BSP was localized in multiple patches scattered throughout the central cellular area. In summary, we found advantages for BSP-coated implant surfaces with regard to osteoinduction, marked differences between recombinant BSP and native BSP when used for implant surface coatings and that the osteointegrating effect of a rough surface can be enhanced by a coating with BSP or fragments thereof which have not been in contact with serum.

The principles of the present invention are useful for implant articles and an endosseous tooth implant, which is composed of a base body, a spacer assembly composed of a spacer bushing bottom or base element and a spacer bushing top or ring member. The base body is provided with an internal bore that has internal threads. The base body adjacent an upper edge or end, has a recess which is of a larger diameter than the bore to provide a stop shoulder. To provide means for preventing axial twisting, the stop shoulder is provided with uniformly, circumferentially spaced recess interlocking pockets so that a ceramic tooth can screwed on.

The invention claimed is:

1. Implant material comprising a substrate selected from the group consisting of titanium, titanium oxide, zirconium, zirconium oxide, tantalum, tantalum oxide, niobium, niobium oxide, magnesium, alloys thereof, and stainless steel, said substrate having been treated with recombinant bone sialoprotein that cannot bind complement factor H or substantive fragments thereof that cannot bind complement factor H.

2. Implant material as claimed in claim 1 wherein the bone sialoprotein is recombinant human bone sialoprotein, recombinant His-Myc-Ek-BSP or substantive fragments thereof.

3. Implant material as claimed in claim 2 wherein the substantive fragments of human bone sialoprotein comprise the RGD sequence.

4. Implant material as claimed in claim 1, wherein the implant material has a surface coating which comprises hydroxyapatite and/or amorphous or nanocrystalline calcium phosphate.

5. Implant material as claimed in claim 1, which has a rough, machined or porous surface structure.

6. Implant material as claimed in claim 5 having pores of 50 to 200 μm diameter size and a pore density of $10^5$ to $10^7$ pores per square centimeter.

7. Implant article made of a coated implant material as claimed in claim 1 which is an endosseous tooth implant, a bone prosthesis, or a bone repair article or matrix.

8. Process of improving the osteointegration properties of implant articles, comprising the step of impregnating the surface of the article with a solution containing recombinant bone sialoprotein that cannot complement factor H, or substantive fragments thereof that cannot bind complement factor H.

9. Process of inducing differentiation of mesenchymal stem cells, proliferation of osteoblast and attachment of cells to an implant material, comprising the step of impregnating the surface with a solution containing recombinant bone sialoprotein that cannot bind complement factor H, or substantive fragments thereof that cannot bind complement factor H.

* * * * *